(12) United States Patent
Ghorbani

(10) Patent No.: US 10,807,017 B2
(45) Date of Patent: Oct. 20, 2020

(54) HEATING FLASH-ON-OIL VAPOR SECTION

(71) Applicant: SCHLUMBERGER TECHNOLOGY CORPORATION, Sugar Land, TX (US)

(72) Inventor: Nasser Ghorbani, Houston, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 16/228,034

(22) Filed: Dec. 20, 2018

(65) Prior Publication Data

US 2020/0197829 A1   Jun. 25, 2020

(51) Int. Cl.
| | | |
|---|---|---|
| *B01D 1/00* | (2006.01) | |
| *B01D 3/06* | (2006.01) | |
| *C07C 29/80* | (2006.01) | |
| *B01D 5/00* | (2006.01) | |
| *B01D 1/02* | (2006.01) | |

(52) U.S. Cl.
CPC ......... *B01D 1/0047* (2013.01); *B01D 1/0082* (2013.01); *B01D 1/02* (2013.01); *B01D 3/06* (2013.01); *B01D 5/0063* (2013.01); *B01D 5/0075* (2013.01); *C07C 29/80* (2013.01)

(58) Field of Classification Search
CPC .. B01D 1/0041; B01D 1/0047; B01D 1/0052; B01D 1/0082; B01D 1/02; B01D 3/06; C07C 29/80
See application file for complete search history.

(56) References Cited

U.S. PATENT DOCUMENTS 5,887,117 A * 3/1999 Desu ................... B01D 1/0082
                                                    392/386
8,623,174 B1 * 1/2014 Duesel, Jr. ............... B01D 1/14
                                                    159/16.1
(Continued)

FOREIGN PATENT DOCUMENTS

KR   1020170019616 A    2/2017
WO   WO 2007/073204   * 6/2007   ............. C07C 29/76
(Continued)

OTHER PUBLICATIONS

International Search Report and Written Opinion issued in the PCT Application PCT/US2019/066233, dated Apr. 10, 2020 (9 pages).

*Primary Examiner* — Renee Robinson
(74) *Attorney, Agent, or Firm* — Hauptman Ham, LLP; Ronald G. Embry, Jr.

(57) ABSTRACT

Method and apparatus for recovering a material by vaporization is disclosed. The method includes providing a heat transfer fluid to a liquid section of a vessel, injecting a material having a first component and a second component into the heat transfer fluid, the first component having a first volatility and the second component having a second volatility greater than the first volatility, circulating the heat transfer fluid from the liquid section to a heat exchanger, heating the heat transfer fluid to a temperature selected to vaporize at least a portion of the second component to a vapor section of the vessel, recovering the vaporized second component from the vapor section of the vessel, and circulating at least a portion of the heat transfer fluid from the from the heat exchanger through the vapor section of the vessel.

17 Claims, 2 Drawing Sheets

(56) References Cited

U.S. PATENT DOCUMENTS

| | | | |
|---|---|---|---|
| 2010/0191023 A1 | 7/2010 | Chen | |
| 2017/0015613 A1* | 1/2017 | King | ........................ C07C 29/80 |
| 2017/0368468 A1* | 12/2017 | Zheng | .................. B01D 1/0094 |
| 2017/0368469 A1* | 12/2017 | Zheng | .................. B01D 1/0041 |
| 2017/0370650 A1* | 12/2017 | Zheng | ........................ F22B 1/02 |

FOREIGN PATENT DOCUMENTS

| | | |
|---|---|---|
| WO | 2011028131 A1 | 3/2011 |
| WO | 2018088650 A1 | 5/2018 |

* cited by examiner

HEATING FLASH-ON-OIL VAPOR SECTION

FIELD

Embodiments of the present invention generally relate to recovery of chemical additives in oil and gas processing. Specifically, methods and apparatus for reclamation of monoethylene glycol from a produced stream are described.

BACKGROUND

In oil and gas production, management of methane hydrates is a challenge. In certain temperature and pressure regimes common during oil and gas production and transportation, methane coordinates with water to produce methane hydrates, which appear as a crystalline solid and can disrupt fluid flow in pipelines, pumps, and compressors. Many methods are used to inhibit and/or counteract the formation of methane hydrates in produced streams. One such method is to use a chemical additive to inhibit formation of methane hydrates. The most commonly used such additive is monoethylene glycol ("MEG"). MEG changes the temperature range at which hydrates form so that the operating temperature of the system does not promote hydrate formation.

Relatively large amounts of MEG must be used to achieve useful results, and MEG is expensive in large quantities. Thus, reclaiming and recycling MEG is economically attractive. Typical processes for reclaiming MEG from produced streams involve flashing MEG, along with water, from the produced stream and then distilling the MEG/water mixture to recover MEG. The flashing process is typically gentle to avoid decomposing the MEG, so equipment that can gently flash large quantities of MEG/water mixture tends to be large. Such equipment is a challenge to accommodate in facilities with limited space, such as offshore oil platforms, so there is a need to reduce the size of MEG reclamation facilities.

SUMMARY

Embodiments described herein provide a method of recovering a material, comprising providing a heat transfer fluid to a liquid section of a vessel; injecting a material having a first component and a second component into the heat transfer fluid, the first component having a first volatility and the second component having a second volatility greater than the first volatility; circulating the heat transfer fluid from the liquid section to a heat exchanger; heating the heat transfer fluid to a temperature selected to vaporize at least a portion of the second component to a vapor section of the vessel; recovering the vaporized second component from the vapor section of the vessel; and circulating at least a portion of the heat transfer fluid from the heat exchanger through the vapor section of the vessel.

Other embodiments described herein provide a method of recovering a material, comprising providing a heat transfer fluid to a liquid section of a vessel; injecting a material having a first component and a second component into the heat transfer fluid, the first component having a first volatility and the second component having a second volatility greater than the first volatility; circulating the heat transfer fluid from the liquid section to a heat exchanger; heating the heat transfer fluid to a temperature selected to vaporize at least a portion of the second component to a vapor section of the vessel; recovering the vaporized second component from the vapor section of the vessel; circulating at least a portion of the heat transfer fluid from the from the heat exchanger through the vapor section of the vessel; condensing a portion of the vaporized second component on the wall of the vessel in the vapor section of the vessel; and sensing a temperature of a wall of the vessel at the vapor section of the vessel.

Other embodiments described herein provide a vaporization apparatus, comprising a vessel having a liquid section and a vapor section, the liquid section having a liquid section wall and the vapor section having a vapor section wall; a feed line fluidly coupled to the liquid section wall; a product recovery line coupled to the vapor section; a recirculation line coupled to the liquid section; a heat exchanger coupled to the recirculation line; a heating coil disposed in the vapor section; and a heat exchanger return line coupled to the heating coil.

BRIEF DESCRIPTION OF THE DRAWINGS

So that the manner in which the above recited features of the present disclosure can be understood in detail, a more particular description of the disclosure, briefly summarized above, is made below by reference to embodiments, some of which are illustrated in the appended drawings. It is to be noted, however, that the appended drawings illustrate only exemplary embodiments and are therefore not to be considered limiting of its scope, may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Figure 1:
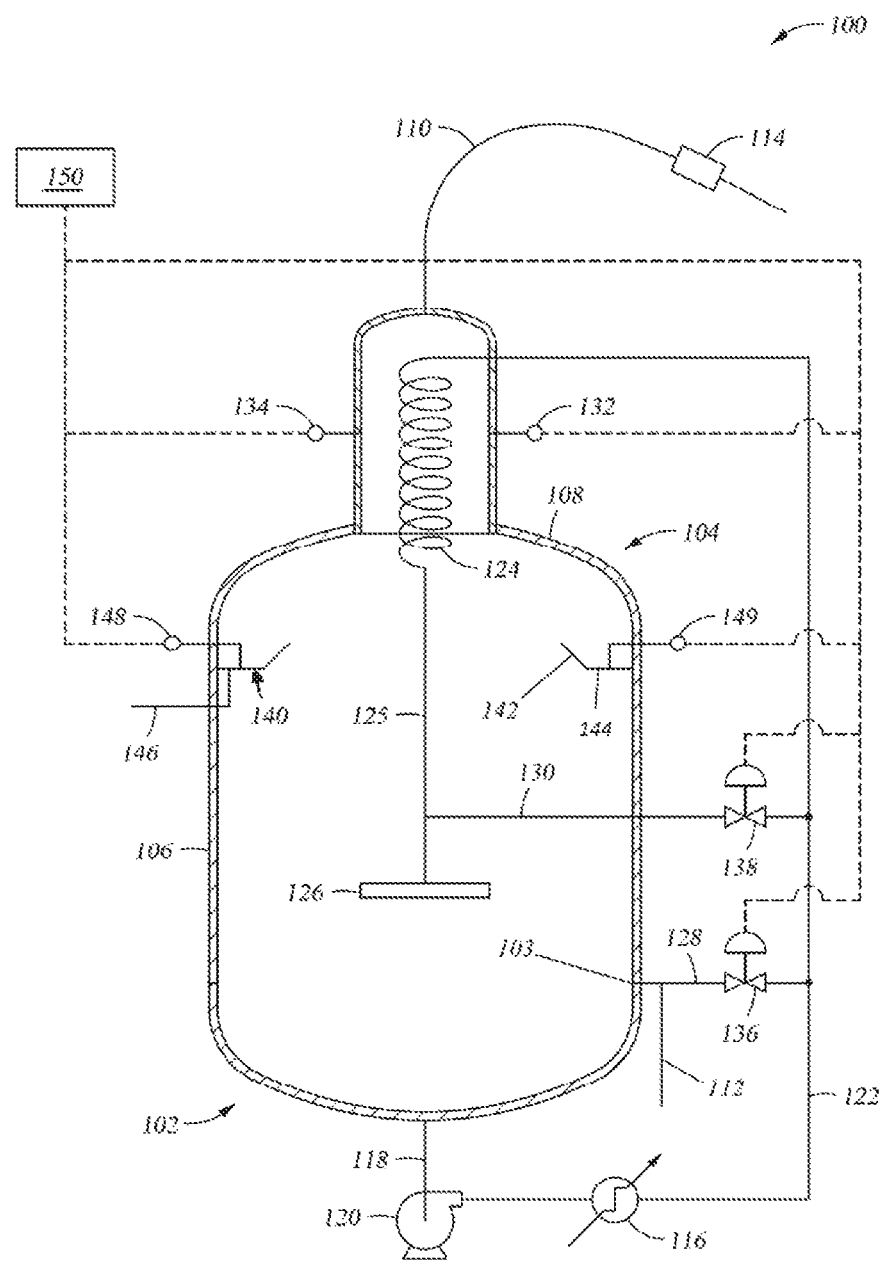
FIG. 1 is a schematic cross-sectional view of a vaporization apparatus according to one embodiment.

FIG. 1 is a schematic cross-sectional view of a vaporization apparatus 100 according to one embodiment. The vaporization apparatus 100 uses direct contact between a heat transfer fluid and a material to be processed. The material is injected directly into the heat transfer fluid to vaporize a portion of the material. The material has at least a first portion and a second portion. The first portion has a first volatility and the second portion has a second volatility higher than the first volatility. The vaporization apparatus 100 has a liquid section 102 and a vapor section 104. For operation the vaporization apparatus is oriented with the vapor section 104 located above the liquid section 102. The liquid section 102 has a liquid section wall 106. The vapor section 104 has a vapor section wall 108. A vaporized product is recovered through a product line 110 coupled to the vapor section 104. The material is provided to the liquid section 102 through a feed line 112 coupled to the liquid section 102 at inlet 103.

A heat transfer fluid is provided to the liquid section 102. The heat transfer fluid is used as a heating medium to vaporize at least a portion of the material provided through the feed line 112. The material is injected directly into the heat transfer fluid at or near the inlet 103, and a portion of the material vaporizes by direct heat transfer from the heat transfer fluid to the material. Vaporized material moves from the liquid section 102 to the vapor section 104, and at least a portion of the vaporized material is recovered through the product line 110. A liquefier 114, such as a condenser or distillation tower, may be coupled to the product line 110 to liquefy the recovered vaporized product.

The heat transfer fluid is heated using a first heat exchanger 116. The first heat exchanger 116 is fluidly coupled to the liquid section 102 by a recirculation line 118 coupled to the liquid section wall 106. A pump 120 may be disposed in the recirculation line 118 to force flow of the heat transfer fluid to the first heat exchanger 116. A return line 122 is also coupled to the first heat exchanger 116 to return the heat transfer fluid to the liquid section 102 by various routes to be described below. Some heat transfer fluid may be returned to the inlet 103 through a first direct return line 128 coupled to the inlet 103. In this case, the feed line 112 is coupled to the first direct return line 128 to inject the feed stream into the flowing heat transfer fluid in the first direct return line 128 such that heat transfer fluid and feed material enter the liquidus of heat transfer fluid in the liquid section 102 together. Alternately, the feed line 112 may be coupled directly to the liquid section wall 106, such that the first direct return line 128 is not coupled to the inlet 103 but returns to the liquidus of the liquid section 102 through a different portal.

A second heat exchanger 124 is disposed in the vapor section 104 of the vaporization apparatus 100. The second heat exchanger 124 provides control over reflux in the vapor section 104 providing localized heating in the vapor section 104 to influence heat loss at the vapor section wall 108 and condensation of a portion of the vaporized material on the vapor section wall 108. The return line 122 is fluidly coupled to the second heat exchanger 124 to flow heat transfer fluid through the vapor section 104 to heat the vaporized material in the vapor section 104. Flow rate and/or temperature of the heat transfer fluid in the second heat exchanger 124 can be used to control a rate of condensation at the vapor section wall 108, or to prevent condensation if desired.

The second heat exchanger 124 may be a straight or coiled tube or pipe located in the vapor section 104, or disposed around the outside of the vapor section 104 near the outer wall thereof. In a coil version, the second heat exchanger 124 may have a constant diameter, which is to say each turn of the second heat exchanger 124 may have the same diameter. Alternately, the diameter of the second heat exchanger 124 may vary. For example, the second heat exchanger 124 may have a profile that follows the shape of the vapor section wall 108. If the vapor section 104 has a diameter that decreases toward the top of the vapor section 104, the second heat exchanger 124 may have a larger diameter in a lower part of the vapor section 104 and a smaller diameter in a higher part of the vapor section 104. The second heat exchanger 124 may be structured and positioned to have a selected clearance between the second heat exchanger 124 and the vapor section wall 108 to provide more intense heat at the vapor section wall 108. Since the vapor section wall 108 is the primary locus of most heat loss and condensation, bringing the second heat exchanger 124 closer to the vapor section wall 108 may provide more energy efficient control of reflux at the vapor section wall 108. For example, in some cases the second heat exchanger 124 may be located about 1-12 inches from the vapor section wall 108, such as about 3 inches. The exact dimension depends on many design parameters, including size and capacity of the vaporization apparatus 100. In alternate embodiments, plate or fin heat exchangers such as radiators may also be used. Additionally, more than one heat exchanger can be used such that the second heat exchanger 124 amounts to a heat exchange assembly comprising a plurality of heat exchangers.

Heat transfer fluid is flowed through the second heat exchanger 124, shown here from top to bottom but bottom to top is also possible. The heat transfer fluid is returned to the liquid section 102 of the vaporization apparatus 100 after flowing through the second heat exchanger 124. Here, a dispenser 126 is coupled to the second heat exchanger 124 by a dispenser conduit 125. The heat transfer fluid releases heat into the vapor section 104 and is reduced in temperature. The first heat exchanger 116 is operated to satisfy the entire heat load of the process, most of which is incurred by vaporizing material in the liquid section 102. Thus the first heat exchanger 116 is typically operated based on a target temperature of the heat transfer fluid in the liquid section 102.

The second heat exchanger 124 may be bypassed by routing the heat transfer fluid through a direct return line, for example the first direct return line 128, to the liquid section 102. A second direct return line 130 may be disposed through the liquid section wall 106 and coupled to the dispenser conduit 125. Depending on the operating level of heat transfer fluid in the liquid section 102, the confluence of the second direct return line 130 and the dispenser conduit 125 may be above the liquidus of the heat transfer fluid or within the liquidus of the heat transfer fluid. The second direct return line 130 may be used to circulate heat exchange fluid through the dispenser conduit 125 and the dispenser 126. The feed line 112 may alternately, or additionally, be coupled to the second direct return line 130.

The vaporization apparatus 100 is designed to control and/or eliminate reflux of material in the vapor section 104 of the apparatus 100. A wall temperature sensor 132 may be coupled to the vapor section wall 108 to monitor reflux conditions. A vapor temperature sensor 134 may also be disposed in the vapor section 104 spaced away from the vapor section wall 108 to monitor vapor temperature in the vapor section 104. A first direct return control valve 136 may be coupled into the first direct return line 128, and a second direct return control valve 138 may be coupled into the second direct return line 130. A controller 150 is operatively coupled to the temperature sensors 132 and 134, and to the control valves 136 and 138 to control circulation of the heat transfer fluid and ultimately the thermal status of the vaporization apparatus 100.

A reflux collector 140 may be disposed along the vapor section wall 108 to collect reflux and to prevent reflux from rejoining the liquid section 102. The reflux collector is an annular trough that extends radially inward from the vapor section wall 108 with a floor 142 of the annular trough and a containment wall 144 that extends upward from the floor 142. Reflux that condenses on the vapor section wall 108 runs down the vapor section wall 108 and collects in the reflux collector 140. A reflux line 146 is coupled to the vapor section wall 108 at a location low in the reflux collector 140 to drain reflux from the reflux collector 140. A reflux level sensor 148 may be disposed in the reflux collector 140 to detect an amount of reflux in the reflux collector 140. A reflux temperature sensor 149 may also be disposed in the reflux collector 140 to detect temperature of the collected reflux. A change in the amount of reflux in the reflux collector 140, other things being equal, usually indicates a change in heat flux through the vapor section wall 108. A change in the temperature of the reflux in the reflux collector 140, other things being equal, usually indicates a change in composition of the reflux. The reflux temperature sensor 149 and the reflex level sensor 148 are operatively coupled to the controller 150 to enhance thermal control of the vaporization apparatus 100.

The vaporization apparatus 100 can be used in an operation to recover MEG from a produced stream. The produced stream containing MEG is charged to the liquid section 102 through the feed line 112, which may be optionally coupled with the first direct return line 128 to mix the returned heat transfer fluid with the produced stream. The level of heat transfer fluid in the reservoir 102 may be above the feed line 112 or below the feed line 112. In such a process, the heat transfer fluid is generally maintained at a temperature above the boiling point of MEG, which is 197° C. at atmospheric pressure. Unfortunately, MEG starts to decompose at temperatures of 163° C., and significant residence time at high temperatures can degrade substantial fractions of the MEG during recovery. Thus, refluxing MEG from the vapor section 104 back to the liquid section 102 can increase exposure time of MEG to high temperatures, and therefore increase MEG decomposition. In conventional vaporization processes, the apparatus may be operated under vacuum to reduce temperature. Using the vaporization apparatus 100, however, because exposure time to temperature is limited, higher temperatures can be used for faster processing.

Figure 2:
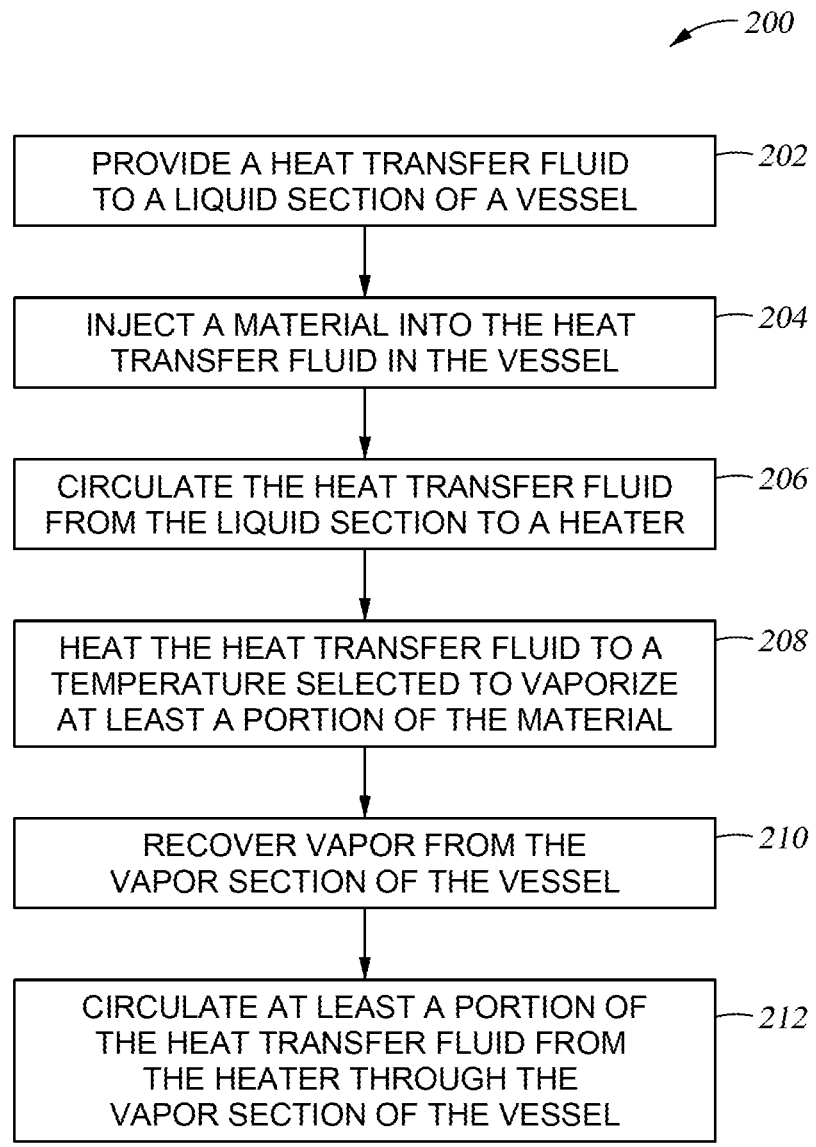
FIG. 2 is a flow diagram summarizing a method according to another embodiment.

FIG. 2 is a flow diagram summarizing a method 200 according to one embodiment. The method 200 is a method of recovering a material by vaporization, which can be used in an overall process of recovering MEG from a produced stream. At 202, a heat transfer fluid is provided to a liquid section of a vessel. The heat transfer fluid is generally a fluid that is immiscible with materials to be recovered from the fluid charged to the vessel. In the case of MEG recovery from a produced stream, the fluid charged to the vessel is a mixture of MEG, water potentially bearing salt, and some residual hydrocarbon, so the fluid used as heat transfer fluid is generally immiscible with MEG and water. The heat transfer fluid is also generally tolerant of high temperatures such as temperatures above the boiling point or flash point of the materials to be recovered in the vaporization process. Such materials generally will not decompose at temperatures at or below the boiling point or flash point of the materials to be recovered. A synthetic aromatic or paraffinic hydrocarbon oil or oil mixture can be used as a heat transfer fluid when recovering MEG by vaporization.

At 204, the material to be processed is injected into the heat transfer fluid in the vessel for processing. The material typically has a first component with a first volatility and a second component with a second volatility greater than the first volatility. In this example, the first component is MEG, or a mixture of MEG and water, and the second component is salty water or heavy hydrocarbon. The vaporization process vaporizes a rich MEG stream containing mostly MEG with a little water, leaving salty water and/or heavier residual hydrocarbon unvaporized.

At 206, the heat transfer fluid is circulated from the liquid section of the vessel to a heat exchanger. The heat exchanger adds heat to the heat transfer fluid to support the entire thermal duty of the apparatus used to perform the method 200. The heat exchanger may be a single stage or multi-stage heat exchanger of any convenient design. If desired, the heat transfer fluid may be filtered or otherwise separated prior to charging to the heat exchanger in order to remove residual unvaporized material, such as salty water, salt crystals, waxes, or other impurities.

At 208, the heat transfer fluid is heated to a temperature selected to vaporize at least a portion of the material. As noted above, the boiling point of MEG is 197° C. at atmospheric pressure. In the method 200, the temperature of the heat transfer fluid exiting the heat exchanger is from about 180° C. to about 220° C. depending on MEG and water content. Although MEG starts to decompose at temperatures as low as 163° C., the method 200 minimizes the time that fluids are exposed to such high temperatures, allowing faster vaporization processing while minimizing degradation of MEG.

At 210, vapor is recovered from the vapor section of the vessel. The vapor is recovered using a vapor line coupled to the vapor section of the vessel. A liquefier, such as a condenser or distillation tower, may be used to liquefy the vapor for easier handling.

At 212, at least a portion of the heat transfer fluid is circulated through the vapor section of the vessel. A portion, or all, of the heat transfer fluid is flowed through the vapor section and thermally contacts the vapor in the vapor section. The heat transfer fluid heats the vapor, adding enthalpy to the vapor and moving it away from its dew point. As the vapor moves through the vapor section, the vapor transfers thermal energy to the walls of the vapor section, losing enthalpy in the process and moving closer to its dew point. The heat from the heat transfer fluid reduces condensation of the vapor. Condensation of the vapor produces reflux in the vapor section. The condensate flows back to the liquid section of the vessel and encounters further residence time at high temperatures, enhancing degradation of MEG in the process. Adding heat in the vapor section reduces or controls reflux such that residence time of MEG in high temperature conditions is managed or minimized.

The heat transfer fluid may be provided to the vapor section of the vessel using any convenient heat transfer device. In one case, a coiled or straight tube may be used to provide thermal contact between the vapor and the heat transfer fluid. In another case, the heat transfer fluid may be flowed through a plurality of hollow plates, or a plurality of tubes having thermal fins.

In some cases, a portion of the vapor may be condensed in the vapor section of the vessel. The flow rate or temperature of the heat transfer fluid provided to the vapor section may be adjusted to change an amount of vapor condensed in the vapor section. Condensing vapor in the vapor section may improve purity of the material of interest in the recovered vapor. For example, condensing a portion of the vaporized MEG stream in a MEG vaporization process may increase the concentration of MEG in the recovered vapor. The condensed vapor usually collects on the walls of the vapor section and runs down the walls. The condensed vapor may be allowed to reflux back to the liquid section of the vessel, or the condensed vapor may be collected prior to refluxing and removed from the vessel to avoid prolonged residence time at high temperatures.

Temperature of the vapor in the vapor section may be measured to determine thermal proximity to the dew point of the vapor. Temperature of the walls of the vapor section may also be measured to monitor heat flux through the vapor section walls. Either temperature, or both temperatures, may be used to set the flow rate and/or temperature of the heat transfer fluid provided to the vapor section of the vessel. For example, if either temperature, or both temperatures meet one or more criteria for determining that condensation of the vapor is excessive, the flow rate and/or temperature of the heat transfer fluid can be increased. If flow rate of the heat transfer fluid is at maximum, and heat needs to be added, temperature of the heat transfer fluid can be increased.

A portion of the heat transfer fluid can be returned directly to the liquid section of the vessel without being routed through the vapor section. Routing a portion of the heat transfer fluid in this manner provides control over the flow rate of heat transfer fluid flowing through the vapor section. Thus, if less flow through the vapor section is desired, more heat transfer fluid can be routed directly to the liquid section, and vice versa.

An amount of condensate or reflux may be measured to determine the thermal balance of the process. A receptacle, such as an annular trough, which may be discrete or continuous, may be disposed along the vapor section wall to collect condensate running down the vapor section wall. The condensate may be removed from the receptacle using a condensate line. A level sensor may be disposed in the receptacle to determine the amount of condensate in the receptacle. Alternately, or additionally, a flow sensor may be disposed in the condensate line to determine the amount of condensate. A change in the amount of condensate, other things being equal, can indicate a change in composition of the vapor moving through the vapor section, which can indicate the need for more or less heat to be added to the process. For example, an increase in the amount of condensate may be met with an increase in the amount of heat added at the heat exchanger, and vice versa.

While the foregoing is directed to embodiments of the present invention, other and further embodiments of the present disclosure may be devised without departing from the basic scope thereof, and the scope thereof is determined by the claims that follow.

What is claimed is:

1. A method of recovering a material, comprising:
providing a heat transfer fluid to a liquid section of a vessel;
injecting a material having a first component and a second component into the heat transfer fluid, the first component having a first volatility and the second component having a second volatility greater than the first volatility;
circulating the heat transfer fluid from the liquid section to a heat exchanger;
heating the heat transfer fluid to a temperature selected to vaporize at least a portion of the second component to a vapor section of the vessel;
recovering the vaporized second component from the vapor section of the vessel;
circulating at least a portion of the heat transfer fluid from the from the heat exchanger through the vapor section of the vessel; and
condensing a portion of the vaporized second component on a wall of the vessel in the vapor section of the vessel.

2. The method of claim 1, further comprising circulating a portion of the heat transfer fluid from the heat exchanger to the liquid section of the vessel.

3. The method of claim 2, further comprising circulating the heat transfer fluid from the vapor section of the vessel to the liquid section of the vessel.

4. The method of claim 3, wherein circulating the heat transfer fluid from the vapor section of the vessel to the liquid section of the vessel comprises flowing the heat transfer fluid through a conduit from the vapor section of the vessel to a dispenser in the liquid section of the vessel.

5. The method of claim 4, wherein the dispenser is immersed in the heat transfer fluid.

6. The method of claim 5, further comprising circulating a portion of the heat transfer fluid from the heat exchanger to the conduit.

7. The method of claim 1, further comprising sensing a temperature in the vapor section of the vessel.

8. The method of claim 1, further comprising sensing a temperature of a wall of the vessel at the vapor section of the vessel.

9. The method of claim 8, further comprising adjusting a flow rate of the heat transfer fluid to the vapor section of the vessel based on the sensed temperature of the wall of the vessel.

10. The method of claim 1, further comprising returning the condensed portion to the liquid section of the vessel, sensing a temperature of a wall of the vessel at the vapor section of the vessel, and adjusting a flow rate of the heat transfer fluid to the vapor section of the vessel based on the sensed temperature of the wall of the vessel.

11. The method of claim 1, further comprising measuring a flow rate of the condensed material and adjusting a flow rate of the heat transfer fluid to the vapor section of the vessel based on the flow rate of the condensed material.

12. A method of recovering a material, comprising:
providing a heat transfer fluid to a liquid section of a vessel;
injecting a material having a first component and a second component into the heat transfer fluid, the first component having a first volatility and the second component having a second volatility greater than the first volatility;
circulating the heat transfer fluid from the liquid section to a heat exchanger;
heating the heat transfer fluid to a temperature selected to vaporize at least a portion of the second component to a vapor section of the vessel;
recovering the vaporized second component from the vapor section of the vessel;
circulating at least a portion of the heat transfer fluid from the heat exchanger through the vapor section of the vessel;
condensing a portion of the vaporized second component on a wall of the vessel in the vapor section of the vessel; and
sensing a temperature of a wall of the vessel at the vapor section of the vessel.

13. The method of claim 12, further comprising adjusting a flow rate of the heat transfer fluid to the vapor section of the vessel based on the sensed temperature of the wall of the vessel.

14. The method of claim 13, further comprising returning the condensed portion to the liquid section of the vessel.

15. The method of claim 13, further comprising measuring a flow rate of the condensed portion and adjusting a target temperature of the wall of the vessel in the vapor section of the vessel based on the flow rate of the condensed portion, wherein adjusting the flow rate of the heat transfer fluid to the vapor section of the vessel is based on a comparison of the sensed temperature of the wall of the vessel to the target temperature.

16. The method of claim 15, further comprising recovering the condensed portion from the vapor section.

17. The method of claim 15, further comprising adjusting a flow rate of the material having the first component and the second component to the vessel based on the flow rate of the condensed portion.

* * * * *